United States Patent [19]

Strayer et al.

[11] Patent Number: 6,051,224
[45] Date of Patent: Apr. 18, 2000

[54] COMPOSITIONS AND METHODS FOR TARGETING CELLS AND MODULATING PULMONARY SURFACTANT SECRETION

[75] Inventors: David S. Strayer, Newtown Square; Avinash Chander, Drexel Hill, both of Pa.

[73] Assignee: Thomas Jefferson University, Philadelphia, Pa.

[21] Appl. No.: 08/602,863

[22] PCT Filed: Aug. 30, 1994

[86] PCT No.: PCT/US94/09752

§ 371 Date: Feb. 28, 1996

§ 102(e) Date: Feb. 28, 1996

[87] PCT Pub. No.: WO95/06665

PCT Pub. Date: Mar. 9, 1995

Related U.S. Application Data

[63] Continuation of application No. 08/176,218, Dec. 30, 1993, Pat. No. 5,674,493, which is a continuation-in-part of application No. 08/114,951, Aug. 31, 1993, abandoned.

[51] Int. Cl.[7] .......................... A61K 39/395; C07K 16/00
[52] U.S. Cl. ..................................... 424/131.1; 424/133.1; 424/134.1; 424/139.1; 424/141.1; 424/143.1; 530/387.2; 530/387.3; 530/388.22
[58] Field of Search .............................. 424/131.1, 133.1, 424/134.1, 139.1, 141.1, 143.1; 530/387.2, 387.3, 388.22

[56] References Cited

U.S. PATENT DOCUMENTS 5,120,525  6/1992  Goldenberg .
5,476,784  12/1995  Rice et al. .

OTHER PUBLICATIONS

Strayer (1991) American J of Pathology (vol. 138(5) 1085–95.
Strayer (1992) Biology of the Neonate vol. 61 Supp 1 2–14.
Robertson et al (May 1992) Eur. J. Pediatrics 151(5):372–6.
D.S. Strayer, Hallman, M. and Merritt, T.A. (1991) Immunogenicity of surfactant. II Porcine and bovine surfactants, *Clin. Exp. Immuno.*, 83, 41–46.
F.M. Ausubel, Brent, R., Kingston, R.E., Moore, D.D., Seidman, J.G., Smith, J.A., and Struhl, K. (eds.) (1991) *Current Protocol in Molecular Biology*, Wiley–Interscience, New York.
Y. Kuroki, Mason, R.J. and Voelker, D.R. (1988) Alveolar type II cells express a high–affinity receptor for pulmonary surfactant protein A, *Proc. Natl. Acad. Sci. U.S.A.*, 85, 5566–5570.
A. F. Guitten, Bougue, B., Mougin, C., Teoule, R. and Bloch, B. (1988) Histological Detection of Messenger RNAs with Biotinylated Synthetic Oligonucleotide Probes, *J. Histochem. Cytochem*, 36, 563–571.
Weinstein et al., "Regional Delivery of Monoclonal Antitumot Antibodies: Detection and Possible Treatment of Lymph Node Metastases", *Cancer Metastasis: Experimental and Clinical Strategies* (Alan R. Liss, Inc.), pp. 169–180 (1986).

*Primary Examiner*—Toni R. Scheiner
*Assistant Examiner*—Geetha P. Bansal
*Attorney, Agent, or Firm*—Law Offices of Jane Massey Licata

[57] ABSTRACT

Methods of modulating pulmonary surfactant secretion and treating conditions such as respiratory distress syndrome, are provided. Compositions for delivering imaging and therapeutic agents through use of the monoclonal antibodies A2C and A2R or fragments thereof are provided. Methods for delivering selected effector molecules such as imaging, modulating and therapeutic agents through use of these compositions are also provided.

8 Claims, 3 Drawing Sheets

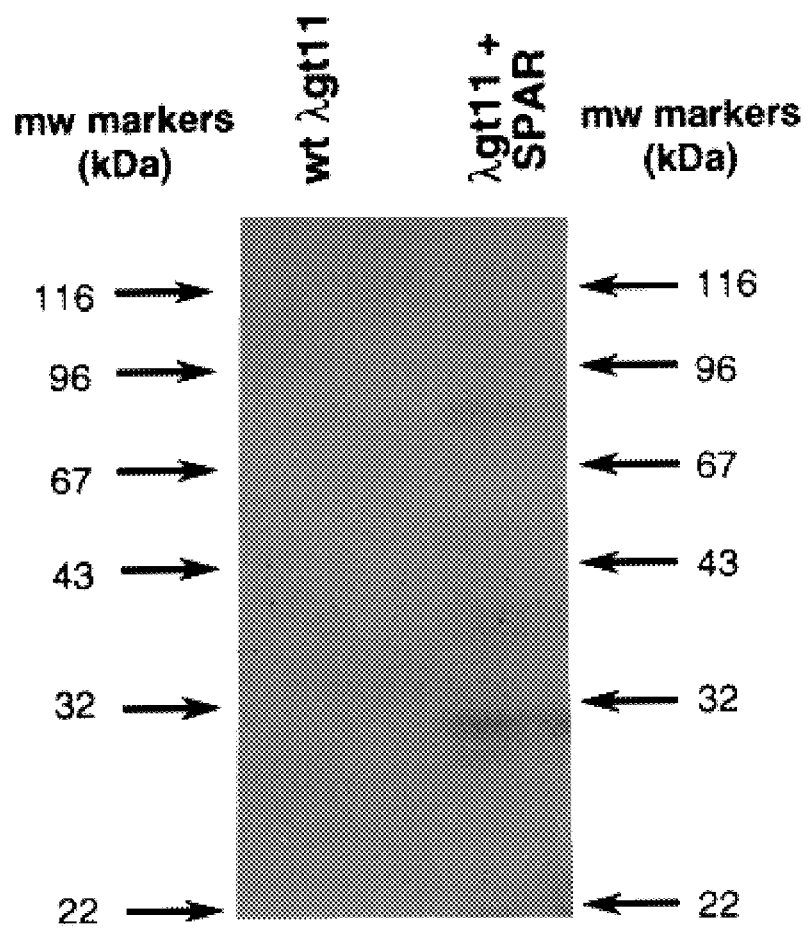
FIG. 3
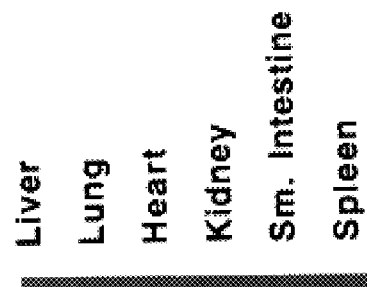
FIG. 4A  SPAR
FIG. 4B  β-actin

SEQUENCE LISTING

<160> NUMBER OF SEQ ID NOS: 4

<210> SEQ ID NO 1
<211> LENGTH: 1820
<212> TYPE: DNA
<213> ORGANISM: Artificial Sequence -continued

```
<220> FEATURE:
<223> OTHER INFORMATION: Description of Artificial Sequence: Porcine
      surfactant protein A recognition protein cDNA

<400> SEQUENCE: 1
cggcgaagag cttcaaagct tggatatttt cttggtgatt cctgaacttg cacaggagct     60
gcatgtgtgg actgataaga gttcactttt cgaagagctt caaagcttgg atattttctt    120
ggctgaactc tacaagcacc ttgacagcag cagcaatgag cgcccagaca ttagctccat    180
ccagagacga ttaagaaag taactcacga catggacatg tgctacggga tgatgggaag     240
cctgtttcgc agtggctccc ggcagaccct cttcgccagc caggtgatgc ggtatgccga    300
tctctatgca gcatctttca tcaatttgct gtattaccca ttcagctacc tcttcagagc    360
tgcccacgtt ttgatgcctc atgagtcaac ggtggaacac acacatgtag atatcaatga    420
aatggagtcc ccctcgcca ccaggaaccg cacgtccgtg gatttcaaag ataccgacta     480
caagcggcat cagttgacac ggtcgattag tgagattaaa ccccccaacc tcttcccact    540 ggcccccaa gaaattacgc attgccatga tgaagatgat gatgaagagg aggaggagga     600
agaggaagaa tgtggtggaa accaaaaact ctcagcactc attaaacaag ttctggcggg    660
actcacagga gcaaaggctg tctctctgtg ggtcctagtg gggggtgggg ggctccatca    720
aaggtacatc ttggaaagtt ttctgaagac tttaaaatat tctaatcata gggagatact    780
tgttttagtt ttttgcatct gcactctttg cagctggttc agaattgtaa gagagtctgt    840
atcggaggag aggaagggtc aagcggggct gaactgcatg cagctggctc cgttgtggtt    900
tgtgacactg tttcatcatc aatatatcat agtgtatcca gaaacacgaa gggtggtgga    960
gggtcccaga gtgaaacaaa gacaatggga agaggtgatc caaaaatgtt atggtacaaa   1020
ttgggctctt actacaaaaa cccatctttt tcagtgcatt acataagtat tgtatatcag   1080
tggagaaatc tattatttcc atgatcaaat gtagtttttt gttaaggtca agttcttttt   1140
acaagctttt aagtgtcctc agggactctg ggaaggctgc tgtcagtggc tctgcagact   1200
gttctctact tactataggg ctggtctgga atggactgca gtgatttcat tttgagccaa   1260
aaatcttcat ccacttctac attttttta accgatagca aaaatgctta ttatccagaa    1320
acctagtctt tttcttatct aggacgaatc tatagaaagg atttcgctga aaggacaaag   1380
gagcaagcca cccaaaagga acagaacctc cttcttacac tgtaactgac caaaattcat   1440
tagcgtgggc tgcatagtgt ggcttatgcc tgccccactc ctcattccag ccttctctat   1500
cctcctgctg tatttcatat tcacgcatta gagggtggga agagatctct ggaagccaga   1560
actgctactc aaacggaggg cacaatgagt gtgaataaat tcactgcaga atcccaagtc   1620
acatcacttc ttgttgttct gaacaagagt gctggatcat tactgtatat tttaaggtat   1680
tataacagcc tcaccagaac agtgaaagct gttacaacat tttccacagt ggtgtagact   1740
cctactttaa ccttcatatg ttttttccag tcttactgtc gtttgtcaac atgggagggt   1800
tgattagctg ttctagaatt                                                1820

<210> SEQ ID NO 2
<211> LENGTH: 1881
<212> TYPE: DNA
<213> ORGANISM: Artificial Sequence
<220> FEATURE:
<223> OTHER INFORMATION: Description of Artificial Sequence: Human
      surfactant protein A recognition protein cDNA

<400> SEQUENCE: 2
```

```
gaccgtgtga ttgtttcaca atttgatgtg tgtgatgata ttagtatgta caatacatgc      60
tgtttacctc tatctagtaa caaatgttta catttgttac tagagtaagc tttaggggta     120
gaacttgagt ctcaaagctc acgtcttggg aaaaaaaaaa gatctggtat tgatagaacc     180
ttgataaatc ccttgttata gcacatgttt ttgtttccca gaagtagggc aagagctctc     240
tggcttatcc aatcagcttc ttctcctgac tttagtagac acacgggctt cattactgag     300
ctgggaattt aacttccctc tgtcctatga aagtagaag attttcctaa gagaaacctt      360
cagtgagagc agaacagaaa aaagagcaaa gaactaactg aaggagaggg caagaaatca     420
gtgtagtgtg gggcagcaga agggaagtga caggtcaaag aaaataggag agaaaaggag     480
agagagctac ccaagtaaac aggaaaaggg gaggaaatac agggcaaaag cagagagcag     540
gggaattggc atgacaagaa agtggtgaaa cacagaggat ccaccagac aacagagagc      600 ccggtagaga agagtgggct aggataaaga gacaggaaac aaatggatta agacatagag     660
tagccattgt cagttacctg ggtaagaaaa gattggtggt ctaaataaaa tgcagattgt     720
tcatttacaa ttctgactgt ttaaattatt tatggtacac cttggtgctt cacttaatca     780
tgttaagtta cagttgtaat cttattaatt acttgcaacc agctttctca atgtaccatg     840
tatagaggac agcttgtcaa ggggtagaag tactatagct tcacttttaa tccagtatca     900
tccagtacac aaattagcct tacactgtta gaatcttcct gatgatgact ggctgaacta     960
agcattagtc ttgacaatac aagtactgct gtgcccattt acagaaaggg aagcaattct    1020
ttcccagaaa gtaagatatg atttaaatgc tttggcctaa ttagctgtga aaaaggacat    1080
ggcccaggta aggcttcagg aaaagccaat taacacatgt gcatatgtct ctctccattc    1140
acatcaccca gcctagtcca agtcaccacc atctcttcac ttgcattgtt acagtagtct    1200
cttagccgct tttcccacct ccacctttga tatctctagt tattcatgag gtccaaaatg    1260 actttaaaa ataacaccac actatctcta tttagacttt tcaacagttt cccactgcac     1320
aagggataca ttaccacaag ggaattacac caacttgccc ttgcaaatct catctttatg    1380
ttcaactgtg ctgatcttca ttttcctcct cagatgcgca aatgctttcc catcccaggg    1440
acttcatgtt tgttctgccc caaaactaaa cactcttcc ctgttcttca tctggctaac     1500
caatatttgt gctttctgtg tcagcataaa cactgttttc ctcagacaag atttcctgac    1560
tcccagccta gccaggccac ttcaaggtgt gtgctctcca taaagtttac ttcttctata    1620
tacatcaatt cacataatta tactttaata cttacttgta taattgttcg tgtgctatgc    1680
cccccagttg gctgtaagtc ctataaagac agaggccaca tccatcttgc acatccctct    1740
gttcctagca cctgccatgg gtcctatcag ctgacaagca ctcaatatat tgtatggata    1800
agtaaatatg attctaattt ccaacatcct aaacttgttt acagtcccac ggagcctgct    1860
caggtagagc acatgcaatg c                                              1881
```

<210> SEQ ID NO 3
<211> LENGTH: 282
<212> TYPE: PRT
<213> ORGANISM: Artificial Sequence
<220> FEATURE:
<223> OTHER INFORMATION: Description of Artificial Sequence: Human
      surfactant protein A recognition protein ORF

<400> SEQUENCE: 3

```
Met Arg Ser Lys Met Thr Phe Lys Asn Asn Thr Thr Leu Ser Leu Phe
  1               5                  10                  15
```

Arg Leu Phe Asn Ser Phe Pro Leu His Lys Gly Tyr Ile Thr Thr Arg
                20                  25                  30

Glu Leu His Gln Leu Ala Leu Ala Asn Leu Ile Phe Met Phe Asn Cys
            35                  40                  45

Ala Asp Leu His Phe Pro Pro Gln Met Arg Lys Cys Phe Pro Ile Pro
        50                  55                  60

Gly Thr Ser Cys Leu Phe Cys Pro Lys Thr Lys Thr Leu Phe Pro Val
65                  70                  75                  80

Leu His Leu Ala Asn Gln Tyr Leu Cys Phe Leu Cys Gln His Lys His
                85                  90                  95

Cys Phe Pro Gln Thr Arg Phe Pro Asp Ser Gln Pro Ser Gln Ala Thr
            100                 105                 110

Ser Arg Cys Val Leu Ser Ile Lys Phe Thr Ser Ser Ile Tyr Ile Asn
        115                 120                 125

Ser His Asn Tyr Thr Leu Ile Lys Thr Cys Ile Val Arg Val Leu
130                 135                 140

Cys Pro Pro Val Gly Cys Lys Ser Tyr Lys Asp Arg Gly His Ile His
145                 150                 155                 160

Leu Ala His Pro Ser Val Pro Ser Thr Cys His Gly Ser Tyr Gln Leu
                165                 170                 175

Thr Ser Thr Gln Tyr Ile Val Trp Ile Ser Lys Tyr Asp Ser Asn Phe
            180                 185                 190

Gln His Pro Lys Leu Val Tyr Ser Pro Thr Glu Pro Ala Gln Val Glu
        195                 200                 205

His Met Gln Cys Phe Leu Cys Met Cys Leu Gln Arg Glu Glu Arg Glu
    210                 215                 220

Ala Leu Leu Leu Pro Arg Val Thr Ile Leu Thr Arg Leu Ser Ala
225                 230                 235                 240

Glu Ser Thr Asp Glu Arg Asp Gly Asp Ser Gly Pro Val Asn Ala Val
                245                 250                 255

Cys Arg Thr Ala Leu Ala Phe Val Pro His Glu Ser Asn Val Met Leu
            260                 265                 270

Gly Ile His Asn Leu Leu Ile Trp Leu Leu
        275                 280

<210> SEQ ID NO 4
<211> LENGTH: 284
<212> TYPE: PRT
<213> ORGANISM: Artificial Sequence
<220> FEATURE:
<223> OTHER INFORMATION: Description of Artificial Sequence: Porcine
      surfactant protein A recognition protein ORF

<400> SEQUENCE: 4

Met Asp Met Cys Tyr Gly Met Met Gly Ser Leu Phe Arg Ser Gly Ser
1               5                   10                  15

Arg Gln Thr Leu Phe Ala Ser Gln Val Met Arg Tyr Ala Asp Leu Tyr
                20                  25                  30

Ala Ala Ser Phe Ile Asn Leu Leu Tyr Tyr Pro Phe Ser Tyr Leu Phe
            35                  40                  45

Arg Ala Ala His Val Leu Met Pro His Glu Ser Thr Val Glu His Thr
        50                  55                  60

His Val Asp Ile Asn Glu Met Glu Ser Pro Leu Ala Thr Arg Asn Arg
65                  70                  75                  80

Thr Ser Val Asp Phe Lys Asp Thr Asp Tyr Lys Arg His Gln Leu Thr
                85                  90                  95

-continued

```
Arg Ser Ile Ser Glu Ile Lys Pro Pro Asn Leu Phe Pro Leu Ala Pro
            100             105             110

Gln Glu Ile Thr His Cys His Asp Glu Asp Asp Glu Glu Glu Glu Glu
            115             120             125

Glu Glu Glu Glu Glu Cys Gly Gly Lys Pro Lys Leu Ser Ala Leu Ile
    130             135             140

Lys Gln Val Leu Ala Gly Leu Thr Gly Ala Lys Ala Val Ser Leu Trp
145             150             155             160

Val Leu Val Gly Gly Gly Gly Leu His Gln Arg Tyr Ile Leu Glu Ser
            165             170             175

Phe Leu Lys Thr Leu Lys Tyr Ser Asn His Arg Glu Ile Leu Val Leu
            180             185             190

Val Phe Cys Ile Cys Thr Leu Cys Ser Trp Phe Arg Ile Val Arg Glu
        195             200             205

Ser Val Ser Glu Glu Arg Lys Gly Gln Ala Gly Leu Asn Cys Met Gln
        210             215             220

Leu Ala Pro Leu Trp Phe Val Thr Leu Phe His His Gln Tyr Ile Ile
225             230             235             240

Val Tyr Pro Glu Thr Arg Arg Val Val Glu Gly Pro Arg Val Lys Gln
            245             250             255

Arg Gln Trp Glu Glu Val Ile Gln Lys Cys Tyr Gly Thr Asn Trp Ala
            260             265             270

Leu Thr Thr Lys Thr His Leu Phe Gln Cys Ile Thr
            275             280
```

COMPOSITIONS AND METHODS FOR TARGETING CELLS AND MODULATING PULMONARY SURFACTANT SECRETION

This is a 371 of PCT 94/09752, filed Aug. 30, 1994 which is a continuation of U.S. Ser. No. 08/176,218, filed Dec. 30, 1993, (now U.S. Pat. No. 5,674,493), which is a continuation-in-part of U.S. Ser. No. 08/114,951 filed Aug. 31, 1993, (now ABN).

INTRODUCTION

This invention was made in the course of research funded by the U.S.P.H.S. (Food and Drug Administration) under grant number FD-R-000461. The U.S. government may have certain rights in this invention.

BACKGROUND OF THE INVENTION

A physiologically active substance, called "pulmonary surfactant" exists in the animal lungs. Pulmonary surfactant is mainly biosynthesized in and secreted from type II epithelial cells of the alveoli and is known to be present as an internal lining of the wall of the whole respiratory tract including the alveolar region. It is known that pulmonary surfactant reduces the surface tension of the alveoli and prevents collapse of the alveoli. In addition, pulmonary surfactant plays an important role as a defense mechanism in the entire respiratory tract. It is well documented that it prevents pulmonary edema and has preventative effects on bacterial or viral infection or on atmospheric pollutants and antigens which induce inflammation of the respiratory tract or asthmatic attacks. Pulmonary surfactant is also known to play an important role in lubricating the respiratory lumen and expelling foreign matter from the respiratory tract by activating mucociliary transport.

Pulmonary surfactant is a complex mixture of proteins and phospholipids. There are four known proteins in alveolar surfactant; SP-A, -B, -C, and -D. SP-B and -C are small, very hydrophobic proteins that interact with phospholipids to lower alveolar surface tension. SP-D is a 43 kDa apoprotein of uncertain function. Like SP-A, SP-D has collagen-like domains. SP-A is a moderately hydrophobic 29–36 kDa apoprotein. It reportedly stabilizes the phospholipid structure and promotes interactions between phospholipids. It also appears to be important in regulating surfactant secretion. These proteins, together with phospholipids, are secreted from alveolar type II pneumocytes and form the air-liquid interphase in the alveoli and comprise what is referred to herein as "alveolar surfactant".

Because of its various physiological functions in the respiratory system, qualitative and quantitative changes of pulmonary surfactant seem to be related to the onset of or aggravation of many conditions. Accordingly, the modulation of secretion of pulmonary surfactant may make it possible to treat or prevent various respiratory conditions, for example acute respiratory failure such as infant or adult respiratory distress syndrome, bronchitis, infectious disease and chronic respiratory failure.

Infantile respiratory distress syndrome which may lead to acute respiratory failure is caused by a deficiency of pulmonary surfactant. A quantitative surfactant deficiency is quite common in preterm infants, causing neonatal respiratory distress syndrome (NRDS). About 10,000–12,000 cases of NRDS occur each year, with mortality of about 15%. Surfactant inactivation, and therefore a relative deficiency in the amount of surfactant secreted by the lung, is thought to be involved in the development of adult respiratory distress syndrome (ARDS). ARDS affects about 50,000–60,000 people in the U.S. yearly and carries a mortality of 50%. Unlike neonatal RDS, for which surfactant replacement therapy is costly but feasible, ARDS is extremely costly to treat in this fashion (requiring up to one hundred times as much surfactant as does NRDS). Thus, new methods of treating ARDS are desired. It has also been reported that in chronic disease associated with respiratory failure, abnormality of pulmonary surfactant may occur.

There is substantial evidence that surfactant secretion is controlled in part by a feedback inhibition circuit involving SP-A and a receptor for SP-A. SP-A inhibits surfactant phospholipid secretion in cultured type II alveolar cells. This inhibition appears to be mediated by a high affinity cell membrane receptor specific for SP-A. Chemical modification of SP-A that alters its interaction with its receptor prevents these effects. Thus, a type II alveolar cell membrane protein that binds surfactant protein A is a major physiologic regulator of pulmonary function. Understanding of this receptor's function and structure permits manipulation of surfactant secretion both in physiological states and in pathologic states when insufficient surfactant is produced (neonatal respiratory distress syndrome: RDS), when surfactant is present in normal amounts but is abnormally inhibited by other proteins (adult RDS), or when surfactant is produced in abnormally large quantities (alveolar proteinosis). Until now, the nature of this binding protein has been unclear.

Monoclonal antibodies have been proposed as a possible means of detecting and treating tumors (Weinstein et al., *Cancer Metastasis: Experimental and Clinical Strategies*, Alan R. Liss, Inc., 1986, pp. 169–80). Monoclonal antibodies specific for identified antigens on the membranes of tumor cells have been used in attempts to direct imaging agents and therapeutics, which often have very detrimental side effects, to the cancerous cells. An advantage of monoclonal antibodies over classical diagnostic agents and treatments is that with monoclonal antibodies it should be possible to specifically target selected cells. Clinical studies with monoclonal antibodies, however, have frequently been unsatisfactory. One of the reasons for this is the difficulty in identifying an antigen found only on a specific target or tissue. Monoclonal antibodies, like all other drugs and therapeutic agents, have little value unless they can be targeted to a specific target or tissue.

The development of two monoclonal antibodies directed against the antigen binding regions of antibodies to surfactant proteins have recently been reported (D. S. Strayer, *Am. J. Pathol.* 1991, 138, 1085–1095 and D. S. Strayer, *Biol. Neonat.* 1992, 61, 1–14). These independently derived anti-idiotype antibodies, A2C and A2R, bind anti-SP-A antibodies and prevent them from binding surfactant protein. These antibodies have been described in terms of their functional characteristics but have not heretofore been structurally characterized. These antibodies may be useful in identifying cell membrane molecules on type II cells that are important in regulating alveolar surfactant secretion. In addition, it has now been found that these antibodies may be used as targeting agents for assisting in the delivery of therapeutic agents to type II cells or bronchial epithelial cells.

SUMMARY OF THE INVENTION

An alveolar cell membrane protein acts as a surfactant protein A receptor (SP-A Receptor); it binds surfactant protein A (SP-A) and regulates alveolar surfactant secretion. Alveolar cell membrane SP-A-binding proteins have been identified using anti-idiotype antibodies directed against the surfactant protein binding region of anti-surfactant antibodies. These monoclonal anti-idiotype antibodies, A2C and A2R, also recognize an alveolar cell membrane protein of approximately 30 kDa. A pulmonary protein of approximately 30 kDa binds SP-A. Unique cDNAs encoding this protein were identified in human (4.1-kilobase) and porcine (1.8-kilobase) lung expression libraries. Coding regions of these cDNA cross-hybridize with each other under stringent conditions. Both cDNAs encode similar approximately 32 kDa proteins that bind SP-A. The human and porcine SP-A recognition (SPAR) proteins resemble each other, as well as other cell membrane receptors. Their projected structures are consistent with cell membrane receptors. Recombinant human and porcine SPA proteins bind SP-A as well as the two anti-idiotype antibodies just as do native lung proteins of approximately 30 kDa. The receptor or SP-A recognition protein (SPAR) transcripts are expressed primarily in lung. The cellular distribution of these transcripts, as determined by in situ hybridization, is similar to that of SP-A protein, as determined by immunohistochemistry; both are found in cells consistent with type II pneumocytes. SPAR-producing cells resemble the alveolar cells expressing SP-B and SP-C transcripts in appearance, location, and distribution. Therefore, cDNAs for pulmonary SP-A-binding proteins from two disparate species have been isolated and sequenced, and the recombinant proteins they encode bind the same ligand.

These anti-idiotype antibodies were used to identify SP-A-binding proteins in human and porcine lung cDNA expression libraries. The ability of these recombinant proteins to bind SP-A is characterized and their cellular expression localized. By virtue of their tissue distribution, their location at type II alveolar cell membranes, their structures, and their ability to bind SP-A, these SP-A recognition proteins (SPAR) appear to be SP-A receptors. This is the first determination of the structure of an SP-A-binding protein in any animal species. The effect of an antibody to an SP-A binding protein on type II alveolar cell membranes on surfactant secretion was tested. The antibody was shown to stimulate secretion. The antibody may be a suitable agent to counteract the inhibition of secretion by SP-A thereby modulating the secretion of alveolar surfactant.

Knowledge of the SP-A receptor, its cDNA and its protein structure may be helpful therapeutically to provide a means to modulate the secretion of alveolar surfactant by controlling the body's own surfactant secretion regulatory apparatus. The cDNA may be used to define the SPAR gene structure and thus characterize potential regulatory compounds that might increase or decrease the cell membrane population of SPAR.

In the present invention, compositions and methods are provided for modulating pulmonary surfactant secretion. In preferred embodiments, monoclonal antibodies are employed to modulate surfactant secretion. An article of manufacture including a pharmaceutical agent and labeling for treatment for conditions characterized by insufficient or excessive surfactant secretion are also contemplated. Such compositions may be useful for conditions such as respiratory distress syndrome.

Compositions and methods are also provided for targeting type II cells or bronchial epithelial cells that also bear the SPAR antigen. In preferred embodiments, the monoclonal antibodies A2C and A2R are employed in combination with a therapeutic agent to target these therapeutic agents to type II or bronchial epithelial cells. Such compositions may be useful in delivery of cytotoxic, sensitizing, radioactive or imaging agents to these cells, in gene therapy of these cells or in directing stimulatory or inhibitory substances to these cells.

DESCRIPTION OF THE DRAWINGS

FIG. 3 is a photograph of binding of A2C and A2R by recombinant SPAR. Wild type λgt11 phage (left) or recombinant phage (right) containing the 4.1 kb human cDNA inset was used to infect E. coli and produce stable lysogeny. Production of the cloned protein was induced with IPTG. The mixture of proteins that resulted, including bacterial proteins, phage proteins, and the protein encoded by the cDNA insert, were harvested and electrophoresed using 10% SDS-PAGE. They were then transferred to PVDF and exposed to A2C and A2r. This was followed by treatment with rabbit and anti-rat Ig, then $^{125}$I-labeled Staphylococcus protein A. Protein sizes were determined from coelectrophoresed molecular mass markers whose locations are shown.

FIG. 4 is a tissue distribution of SPAR RNA. Equal quantities of whole RNA from various rabbit organs were blotted to nitrocellulose filters and probed with cloned porcine SPAR cDNA (left) and actin (right). Hybridization was performed under relaxed conditions (40% formamide, 37° C.). Final washes were of moderate stringency (0.4× SSC, 42° C.). For both probes, the order of the organs represented is as follows (from left to right): liver, lung, heart, kidney, small intestine, and spleen.

DETAILED DESCRIPTION OF THE INVENTION

Figure 1:
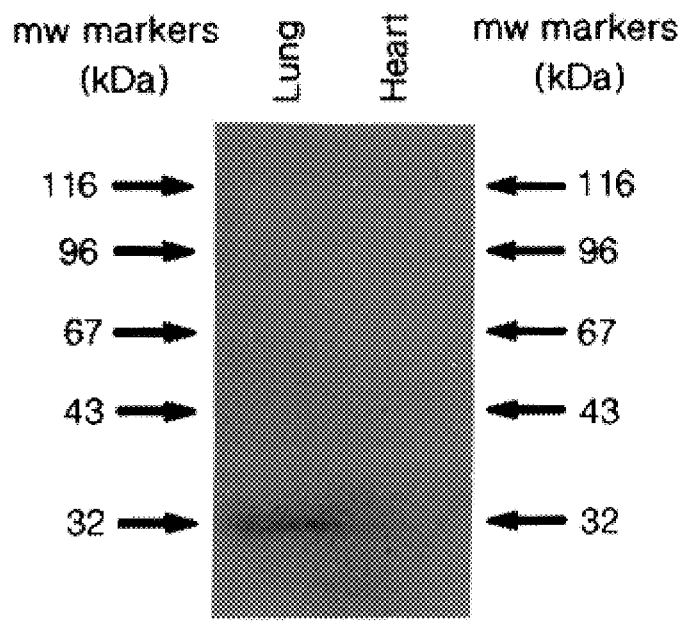
FIG. 1 is a photograph of SP-A binding activity in lung homogenates. Lung (left) and heart (right) tissues from normal rabbits were homogenized. Proteins were electrophoresed using 10% SDS-PAGE under reducing conditions, transferred to PVDF membrane, and exposed to $^{125}$I-SPA-binding protein (approximately 30 kDa) was determined by comparison with coelectrophoresed marker proteins, whose sizes are shown at the sides of the autoradiograph.

As used herein, "alveolar surfactant protein" refers to the apoproteins associated with alveolar surfactant described herein below. The human lung is composed of a large number of small sacs or alveoli in which gases are exchanged between the blood and the air spaces of the lung. The exchange is mediated by the presence of alveolar surfactant which is a complex substance that lines the epithelial surface of the lung. The surfactant is composed of phospholipid components and protein components. The surfactant-associated protein comprises both serum protein and surfactant-specific apoproteins. There are three major surfactant-specific proteins One is a water-soluble protein having a molecular weight of 29–35 kDa (alveolar surfactant protein SP-A) and the other two are very hydrophobic proteins having molecular weights of 9 kDa (SP-B) and 3.5 kDa (SP-C). Granular pneumocytes (type II alveolar cells) secrete the surfactant material.

"Alveolar surfactant protein SP-A" refers to the relatively high molecular weight (29–35 kDa) apoprotein associated with the pulmonary surfactant. The nucleic acid sequence of SP-A is known.

Regulation of alveolar surfactant production has been the subject of considerable investigation. Both physical and chemical stimuli reportedly alter surfactant release by type II epithelial cells of the alveoli. However, different studies have examined different parameters (phospholipid production, phospholipid secretion, secretion of SP-A or SP-B, levels of transcripts for one or more surfactant proteins, etc.) in different experimental systems (human, animals, organ or cell culture, tissue treated in vivo but examined ex vivo, etc.). Each approach has strengths and weaknesses, and different approaches have yielded different results.

The best studied stimuli for alveolar surfactant secretion are pharmacologic doses of corticosteroids. In general, glucocorticoid administration accelerates pulmonary maturation in utero, and SP-A, -B, and -C expression production and expression in adult animals. However, the effects of dexamethasone on SP-B and -C expression differ in magnitude, timing and direction from its effects on SP-A suggesting that steroids regulate SP-B and -C expression fundamentally differently from SP-A expression.

Other cytokines, pharmacologic agents, and mediators have been reported to increase or decrease surfactant synthesis. To the extent that their modes of action are understood, these agents act through many different mechanisms. In some cases, e.g., phorbol esters, both increased and decreased SP-A and -B expression have been reported.

This abundance of data (some reports contradicting others) regarding pharmacologic influences on surfactant production underscores the need for understanding the physiologic regulation of surfactant production. Identification of an SP-A receptor on type II alveolar cells is thus important in developing methods to modulate alveolar surfactant production.

Anti-idiotype antibodies were used to identify a non-Ig cell membrane protein that binds SP-A. Use of anti-idiotype antibodies is predicated on the premise that if two molecules (in this case anti-SP-A antibody and SP-A receptor) bind the same ligand (SP-A), their ligand binding sites may be similar. A variety of cell membrane receptors have been characterized using this approach. Thus, to identify SP-A receptor, a group of monoclonal antibodies (Mabs) that bind surfactant protein were used. Many of these Mabs both bind SP-A and inhibit its function. This population undoubtedly possesses a diverse range of idiotypic regions. One or more of their SP-A binding regions could mimic the SP-A receptor ligand binding site.

Two rats immunized independently with different combinations of monoclonal anti-SP-A antibodies produced anti-idiotype antisera that recognized SP-A-binding sites of different anti-SP-A Mabs. From these animals, two monoclonal anti-idiotype antibodies were produced. Each of these bound anti-surfactant antibody and prevented surfactant binding by anti-surfactant antibody. The antibodies, A2R and A2C, also both recognize the same approximate 30 kDa non-Ig protein on rabbit, pig, and human alveolar cell membranes and inhibit surfactant binding by these cells. Simultaneously, an approximately 31 kDa pulmonary protein binds recombinant SP-A. A2R and A2C bind a protein on the cell membranes of alveolar and bronchial cells but not macrophages, lymphocytes, and other cells. When cellular surfactant binding capacity is saturated by preincubating cells or tissue sections with surfactant, A2C and A2R no longer bind these cells. Thus, A2C and A2R MaAbs and surfactant protein all bind the same cell membrane structure.

The structure of two independently isolated cDNAs from different animal species have now been characterized. These cDNAs were identified, because A2R and A2C recognized their protein products. The coding regions of these cDNAS resemble each other closely. The ORFs they encode are remarkably similar in size and are close to the observed size of the SP-A-binding cell membrane protein and the protein recognized by A2C and A2R. The human and porcine ORFs are homologous to each other. They have comparable secondary structures, both consistent with cell membrane receptors. The recombinant proteins that are encoded by these cDNAs are similar in size, bind A2R and A2C, and recognize purified recombinant SP-A. Thus, these alveolar cell membrane proteins are SPAR proteins.

A2C and A2R also weakly bind higher molecular weight species present in Y1089 cells infected with recombinant, but not wild type, λgt11. The larger species may be a multimer or aggregate of SPAR protein or may alternatively represent aberrant transcripts or a larger SPAR protein in which a translational stop signal has been ignored.

The distribution of SPAR transcripts is consistent with their origin in type II alveolar cells. Immunohistochemical analysis and in situ hybridization studies indicate that SPAR is expressed in prominent and protruding alveolar cells, usually located at corners of alveoli. The same location is seen in the alveolar cells that express SP-B and SP-C and is consistent with and characteristic of type II alveolar pneumocytes. Cells that make SPAR transcripts and proteins are not consistent in appearance or location with type I pneumocytes, alveolar macrophages, interstitial cells, or stromal cells. These observations indicate that SPAR is made by type II pneumocytes. Unlike SP-B and SP-C, SPAR is also expressed in ciliated airway lining cells but not, apparently, in Clara cells, suggesting that SPAR (or a like protein) may have functions in several cell types.

Therefore, SPAR proteins are SP-A recognition structures on alveolar cells. They may represent the whole SP-A receptor or only an SP-A binding portion thereof. The data indicate that blocking SPAR-SP-A interactions in vivo with A2C or A2R increases levels of SP-A transcripts. Thus, SPAR proteins are alveolar type II cell membrane SP-A-binding proteins and appear to be the ligand binding structures of the alveolar type II cell SP-A receptor.

Pulmonary surfactant secretion from alveolar epithelial type II cells can be stimulated with a wide variety of agents, including isoproterenol and ATP. Purified SP-A inhibits secretion of lung surfactant in vitro. The effect of an antibody to an SP-A binding protein on type II cell membranes on surfactant secretion was tested. Results indicated that the A2C and A2R monoclonal antibodies specifically interfered with SP-A mediated inhibition of surfactant secretion making them suitable agents to counteract the inhibition of secretion by SP-A.

Knowledge of the SP-A receptor, its cDNA and its protein structure may be helpful therapeutically to provide a means to modulate alveolar surfactant secretion by controlling the body's own surfactant secretion regulatory apparatus. In addition, knowledge of these antibodies and their specificity for type II cells and bronchial epithelial cells containing the SP-A receptor, is useful in targeting therapeutic agents to the lung. In the present invention, the term "therapeutic agent" refers to any molecule or group of molecules expected to have an effect upon or produce some change in the targeted cells. The potential therapeutic possibilities are considerable. Only a few will be recounted here.

For example, synthetic receptor protein may be instilled to prevent SP-A recognition by SPAR, thus potentially enhancing surfactant secretion. In addition, receptor analogs (perhaps more efficient in binding SP-A) may be used in the same mode. The cDNA may be used to define the SPAR gene structure and thus characterize potential regulatory compounds that might increase or decrease the cell membrane population of SPAR, thereby regulating the production of SP-A. Therapeutic agents can be conjugated to at least one chain of the A2C or A2R antibody and targeted to type II cells. While the number of therapeutic agents is considerable, only a few will be recounted here.

In one embodiment, the therapeutic agent comprises a chemotherapeutic agent. For example, an individual afflicted with a tumor of bronchial or type II cell origin may be amenable to therapy in which either the A2C or A2R antibody is complexed to or used to direct through a vehicle such as liposomes a cytoxic or radioactive agent to the tumor cells. In another embodiment, these antibodies are conjugated to a sensitizing agent which, when combined with another therapeutic modality, could improve the specificity of a cytotoxic therapy for tumors of type II or bronchial epithelial cells.

These antibodies could also be used in imaging. Clinical pulmonologists or neonatologists often have a need to determine functional type II cell mass and/or distribution. In this embodiment, at least one chain of one or both of the antibodies are attached to a radiologically active substance and used to localize the radiologically active substance to type II cells. Examples of radiologically active substance include, but are not limited to, radionucleides used for conventional imaging such as $^{99m}$Tc and radionucleides used in magnetic resonance imaging such as $^{13}$C. The localized radioactivity can then be quantitated or visualized by techniques well known to diagnostic radiologists or nuclear medicine physicians.

The antibodies are also useful in the direction of stimulatory or inhibitory substances such as tumor necrosis factor, PGE, TGFB, IL-6, terbutaline cyclic nucleotides, to type II or bronchial epithelial cells. In this embodiment, a stimulator or inhibitor which are referred to herein as a "modulating agent", may be specifically targeted to a selected cellular target. For example, a cytokine that stimulates surfactant production, but is toxic to many cells at the required therapeutic concentration, is incorporated into a delivery vehicle such as a liposome which has one or both antibodies attached. This vehicle-antibody combination permits delivery of a high concentration of the toxic cytokine to the specific cellular target. Thus, agents intended to inhibit or stimulate the target cell function can be delivered specifically to these target cells without the adverse complications and unwanted side effects often associated with such agents.

These antibodies could also be used in gene therapy of type II cells. In some diseases such as congenital alveolar proteinosis, it has been established that afflicted individuals are deficient in a surfactant protein. This deficiency appears to reflect a genetic defect in the gene in question. Gene replacement targeted at type II cells could correct this deficiency. One method for carrying out this gene therapy is to clone the surfactant protein P gene or its cDNA from either the gene's own promoter or from another promoter. This construct is then incorporated into liposomes or engineered vectors which are targeted to type II cells through one or both of the A2C or A2R antibodies. The liposome or vector containing the construct can then be administered so that the construct can be incorporated into the targeted cells with the intent of rectifying the deficiency.

These antibodies could also be applied to gene therapy by redressing transient but life-threatening deficiencies in surfactant or other type II cell product. A liposome, targeted using A2C and/or A2R, could be used to insert a surfactant protein gene controlled by a powerful promoter into type II cells in order to induce the synthesis of large amounts of surfactant.

A2R and A2C could also be used to target stimulatory or inhibitory agents to the bronchial epithelium that bears SPAR-like protein on its cell membrane. Thus, for example, if an agent is found that can modulate bronchial mucous secretion, A2R and/or A2C could be used to target such an agent to the bronchial epithelium to decrease or increase mucous secretion. Such an agent might be used, for example, to decrease mucous secretion in chronic bronchitis or asthma.

Antibodies and antibody fragments are encompassed by the instant invention. "Antibody fragments" which contain the idiotype of the molecule can be generated by well known techniques. For example, such fragments include but are not limited to the F(ab')$_2$ fragment which can be produced by pepsin digestion of the antibody molecule; the Fab' fragments which can be generated by reducing the disulfide bridges of the F(ab')$_2$ fragment; and the F(ab) fragments which can be generated by treating the antibody with papain.

It is also contemplated that humanized antibodies can be produced and utilized in the present invention. Nonhuman antibodies can induce an immune response in humans. Recombinant DNA techniques minimize this problem by "humanizing" nonhuman monoclonal antibody (MAb) genes. The productively rearranged IgG genes of the hybridoma can be identified by Southern blot analysis by comparison of the patterns of hybridizable bands obtained from restricted DNA of the hybridoma and its parent myeloma using V region probes for the light and heavy chain genes. Size-fractionated DNA containing the productively rearranged genes can be cloned into lambda phage and identified by screening with V region probes. Subsequently, the variable region of the cloned genes can be subcloned into a plasmid containing the human constant region genes. Further humanizing of the nonhuman-human chimeric antibody genes may be achieved by oligonucleotide site-directed mutagenesis. Oligonucleotides containing the sequence coding for human framework regions with flanking nonhuman sequences can be annealed to the nonhuman-human antibody plasmids, transfected into *E. coli*, and mutated plasmids identified by hybridization with oligonucleotides. By this approach, nonhuman framework sequences would be converted to human sequences so that only the complementarity determining regions (CDRs) will contain the nonhuman sequence. Plasmids containing the humanized genes can be expressed by the transfection of light and heavy chain genes into a nonhuman non-producing myeloma cell line, for example.

As used herein, the term "antibody" is meant to refer to complete, intact antibodies, Fab fragments, and F(ab)$_2$ fragments. It is preferred that antibodies be complete, intact antibodies. The protein structure of complete intact antibodies, Fab fragments and F(ab)$_2$ fragments and the organization of the genetic sequences that encode such molecules are well known.

As used herein, the term "chimeric antibody" is meant to refer to antibodies which consist of a constant region from an antibody derived from a first species and a variable region in which either the entire variable region or at least a portion of the variable region is derived from a second species.

As used herein, the term "hybrid variable region" refers to a variable region that comprises portions derived from at least two different species. Generally, a hybrid variable region consists of framework sequences from one species and CDRs from a different species.

As used herein, the term "humanized antibodies" is meant to refer to chimeric antibodies that comprise constant regions from human antibodies and hybrid variable regions in which most or all of the framework sequences are from a human variable region and all or most of the CDRs are from a nonhuman variable region. Chimeric antibodies are produced by well known recombinant techniques and readily available starting materials. Such techniques are described, for example, in UK Patent Application GB 2,188,638 A.

Antibodies, or fragments thereof, can be therapeutically administered at selected concentrations to bind to the SP-A receptor. In a preferred embodiment, compositions comprising one or both of the A2C and A2R antibodies or fragments thereof in combination with a selected effector can be administered at selected concentrations to bind to the type II cells or bronchial epithelial cells. Various delivery systems can be used for therapeutic delivery of the antibody or antibody fragments. Methods of introduction include but are not limited to intradermal, intramuscular, intraperitoneal, intravenous, subcutaneous, and intranasal routes. Also, intratracheal or intrabronchial administration as aerosol is contemplated. The antibody can also be encapsulated in liposomes. Various pharmacologic compositions may be utilized in order to deliver the antibodies or fragments thereof. Any suitable pharmaceutical agent with desirable solubility characteristics and chemical properties may be used, including but not limited to, where appropriate, saline or dextrose.

Compositions of the present invention may also be combined with a vehicle. "Vehicle", as used herein, means a substance, usually without therapeutic action, used as a medium for the administration of a therapeutic or modulating agent.

Compositions comprising at least one chain of an A2C or A2R monoclonal antibody or a fragment thereof and a selected effector are provided. The selected effector comprises a therapeutic agent, an imaging agent or a modulating agent. In one embodiment, a composition comprising the antibody and a therapeutic agent, such as a cytotoxin or a gene replacement construct, is prepared, either alone or in combination with a sensitizing agent. In another embodiment, the antibody is combined with a selected imaging agent such as $^{99m}$Tc or $^{13}$C. In yet another embodiment, the antibody and a selected modulating agent, such as a cytokine, are administered either alone or in combination with a selected vehicle.

"Therapeutic agent" as used herein refers to an agent which is a biologically-active synthetic or natural substance, other than alveolar surfactant proteins themselves, that is useful for treating a medical or veterinary disorder or trauma, preventing a medical or veterinary disorder, or regulating the physiology of a human being or animal. Preferred pharmaceutical agents are those which are useful in treating disorders localized in or near the lungs or respiratory tract, such as infant or adult respiratory distress syndrome, oxygen toxicity associated with respirator therapy, pneumonia, bronchitis, asthma, emphysema, tuberculosis, chronic obstructive pulmonary disorders, and lung cancer.

"Respiratory distress syndrome" includes many conditions characterized by respiratory distress or failure, including but not limited to the following: shock; traumatic shock; Gram negative septic shock; sock due to other infectious organisms besides Gram negative bacteria; toxic shock; fluid loss or blood volume depletion other than traumatic shock; allergic reactions; allergic reactions to inhaled allergens; allergic reactions to ingested allergens; allergic reactions to administered allergens (either iatrogenically or otherwise); pneumonitis or pneumonia due to infectious agents; pneumonitis or pneumonia due to infectious agents where the infectious agent is bacterial; pneumonitis or pneumonia due to infectious agents where the infectious agent is fungal; pneumonitis or pneumonia due to infectious agent is a protozoan; pneumonitis or pneumonia due to infectious agents where the infectious agent is a multicellular organism; pneumonitis or pneumonia due to infectious agents where the infectious agent is mycoplasma; pneumonitis or pneumonia due to infectious agents where the infectious agent is *Pneumocystis carinii*; toxic pneumonitis; toxic pneumonitis where the toxin is inhaled; toxic pneumonitis where the toxin is ingested; toxic pneumonitis where the toxin is injected; toxic pneumonitis where the toxin is applied topically; primary organ failure in an organ other than the lungs; primary organ failure in an organ other than the lungs where that organ is the heart; primary organ failure in an organ other than the lungs where that organ is the liver; primary organ failure in an organ other than the lungs where that organ is the kidneys; primary organ failure in an organ other than the lungs where that organ is the digestive system; primary organ failure in an organ other than the lungs where that organ is the endocrine system (e.g., thyroid, adrenal, parathyroid); a reaction to an administered pharmacologic agent, including administered blood or blood products, pharmaceuticals and anesthetics; a tumor, benign or malignant, of the lungs or other organs; a developmental abnormality, including immaturity of the lungs; a developmental abnormality, including immaturity of the cardiovascular system; a developmental abnormality of the chest or chest wall; a developmental abnormality of the diaphragm; a developmental abnormality, including immaturity, of the digestive system; ionizing radiation.

Methods of delivering the selected effectors to cells whose surfaces bear the SPAR antigen are also provided. In these embodiments, at least one chain of an A2C or A2R monoclonal antibody or a fragment thereof is complexed with the selected effector. The antibody-effector complex is then contacted with the targeted cells having SPAR antigens on their surfaces. In this way, the selected effectors are effectively delivered to the cells.

Kits for practice of the instant invention are also provided. Therapeutic kits comprise the therapeutic composition (pharmaceutical agent) of the invention in one or more containers and appropriate labeling.

Additionally, the invention encompasses novel peptides and polypeptides which are recognized by and bind to SP-A receptor. As is the case for all proteins, a protein within the scope of the invention can occur in neutral form or in the form of basic or acid addition salts depending on their mode of preparation, or, if in solution, upon its environment. It is well understood that proteins in general, and, therefore alveolar surfactant proteins, in particular, may be found in the form of their acid addition salts involving the free amino groups, or basic salts formed with free carboxyls. Pharmaceutically acceptable salts may, indeed, enhance the functionality of the protein. Suitable pharmaceutically acceptable acid addition salts include those formed from inorganic acids such as, for example, hydrochloric or sulfuric acids, or from organic acids such as acetic or glycolic acid. Pharmaceutically acceptable bases include the alkali hydroxides such as potassium or sodium hydroxides, or such organic bases as piperidine, glucosamine, trimethylamine, choline, or caffeine. In addition, the protein may be modified by combination with other biological materials such as lipids and saccharides, or by side chain modifications, such as acetylation of amino groups, phosphorylation of hydroxyl side chains, or oxidation of sulfhydryl groups or other modification of the encoded primary sequence. Indeed, in its native form, the alveolar surfactant protein SP-A is a glycosylated protein, and certain of the encoded proline residues have been converted to hydroxyproline. Included within the definition of alveolar surfactant protein SP-A are glycosylated and unglycosylated forms, hydroxylated and non-hydroxylated forms, and any composition of an amino acid sequence substantially similar to that of the native sequences which retains activity. Also included within the definition are fragments of the entire sequence which retain activity. Also encompassed are novel conjugates in which a peptide or polypeptide of the invention is attached, either directly or via a linker moiety, to a second compound. The conjugates include, but are not limited to fusion proteins and polypeptides containing the novel peptides and polypeptides.

RESULTS

SP-A Binding Activity in Lung Homogenates

A2C and A2R anti-idiotype monoclonal antibodies both bind a 30 kDa alveolar cell membrane protein in three different animal species. Proteins from rabbit lung (and heart, as a negative control) were electrophoresed using SDS-PAGE, blotted to PVDF and treated with $^{125}$I-labeled purified recombinant human SP-A to ascertain if a lung protein of similar size also binds SP-A. A lung protein of approximately 30 kDa binds SP-A (FIG. 1). Thus, normal lung proteins of approximately 30 kDa bind SP-A and A2C and A2R anti-idiotype antibodies.

Identification and Characterization of cDNAs Encoding Human and Porcine SP-A-binding Proteins A2C and A2R were then used to identify cDNA clones encoding SPAR. The antibodies were used in combination to screen human and porcine lung cDNA expression libraries in λgt11. About $10^6$ plaques from each library and 11 in the human library bound A2C and A2R. However, each library yielded only one unique clone that encoded a protein recognized by A2C and A2R. The cDNA inserts were 1.8 kb (porcine) and 4.1 kb (human).

Binding of SP-A by the Cloned Proteins

Figures 2A, 2B:
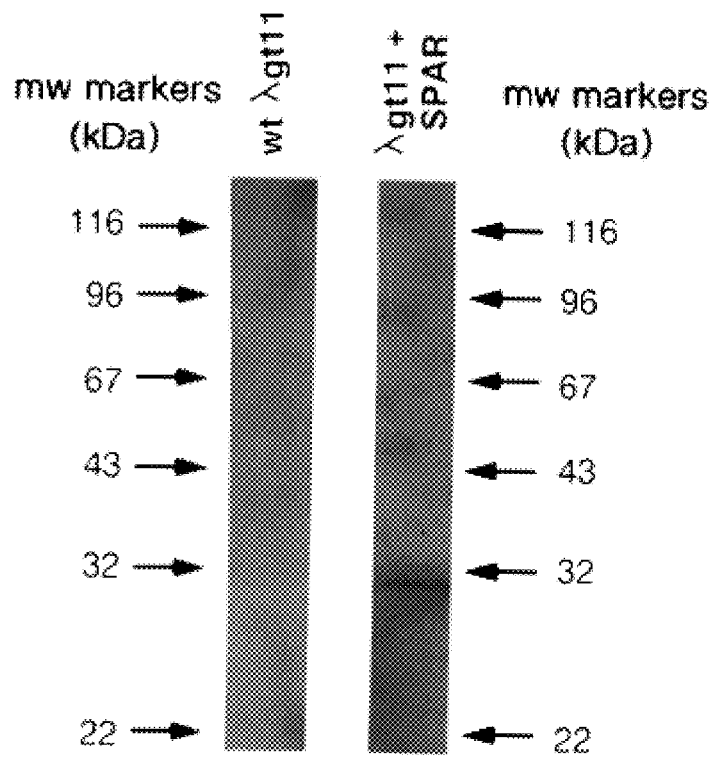
FIG. 2 is a photograph of binding of SP-A by recombinant SPAR. Wild type λgt11 phage (left) or recombinant phage (right) containing the 4.1-kb human cDNA inset was used to infect E. coli and produce lysogenic colonies in which phage stably infected Y1089 cells. IPTG was used to induce production of the cloned protein. The resultant mixture of proteins included a combination of bacterial proteins, phage proteins, and the protein encoded by the cDNA insert. These were harvested, electrophoresed using 10% SDS-PAGE, transferred to PVDF, and exposed to 125I-labeled human SP-A. The size of recombinant SP-A-binding protein was ascertained from coelectrophoresed molecular mass markers whose molecular sizes are shown.
Figure 5A:
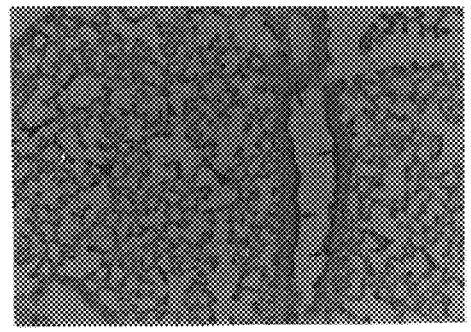
FIG. 5 uses 1.8-kb SPAR cDNA as probe, normal BALB/c mouse tissues were examined by in situ hybridization for SPAR transcript. mRNA for SPAR found in bronchial (liver, spleen, heart, kidney) tissues did not express detectable SPAR. These results regarding mRNA detection corroborate our immunohistochemical experiments in which A2C and A2R were used to detect SPAR protein in tissue sections.
Figure 5B:
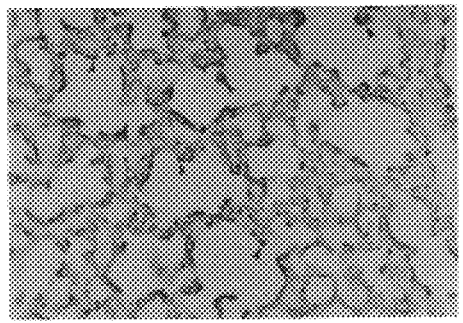
Figure 5C:
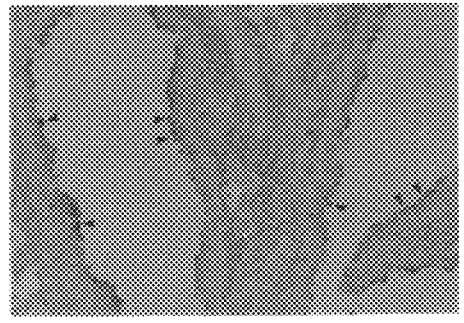
Figure 5D:
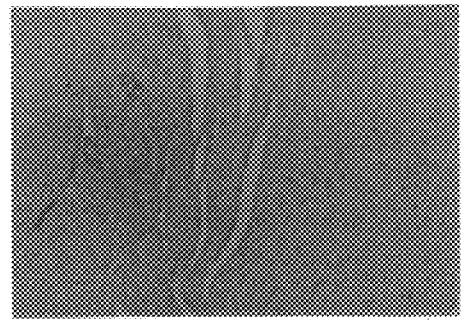
Figure 5E:
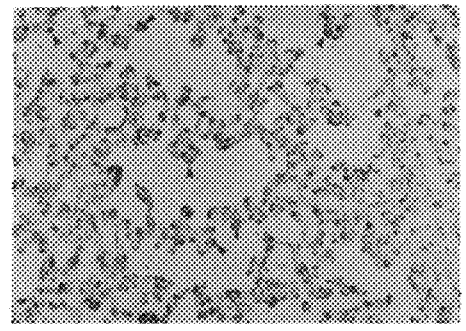

The proteins encoded by these cDNA clones were analyzed for their ability to bind SP-A. In lysogenic phage colonies, IPTG was used to induce expression of the cloned protein. Proteins were prepared from these lysogeny, and their ability to bind SP-A was tested (FIG. 2). The results shown are for the 4.1 kb human cDNA, but identical results were obtained using its porcine counterpart. An approximately 31 kDa protein encoded by the cDNAs and expressed in λgt11 binds radiolabeled SP-A. *Escherichia coli* infected with wild type λgt11 show no such SP-A binding activity.

Simultaneously, it was ascertained that the anti-idiotype MaAbs principally recognize proteins of similar size in these preparations (FIG. 3). A2R and A2C also slightly bind higher molecular weight species in these, but not control, preparations. Preparation expressing the approximate 31 kDa protein from the porcine 1.8 kb cDNA reacted similarly.

Structure of the cDNA and Their Encoded Proteins

The porcine and human SPA cDNAs were sequenced, and the structures of the encoded proteins deduced. The two SPAR cDNA sequences are 40% identical. Both cDNAs, but particularly the human SPA cDNA, include substantial untranslated 5' and 3' segments. The cDNA of hSPAR and pSPAR are highly homologous, but principally in their coding regions (opt=594). The 5'- and 3'- untranslated regions are divergent. This was confirmed by Southern analysis using SPAR cDNA subfragments. Table I shows the aligned human and porcine SPAR cDNAs.

Table I

Sequence Homologies between Human and Porcine SPAR cDNAs

```
  1 ...CGGCGAAGAGCTTCAAAGCTTGGATATTTTCTTG...GTGATTCCTGA  45
          ||    |   |  ||||  |   |||     |  |   ||    |  |  |       |
801 GACCGTGTGATTGTTTCACAATTTGATGTGTGTGATGATATTAGTATGTA 850

46 ACTTGCACAGGAGCTGCATGTGTGGACTGATAAGAGTTCACTTTTCGAAG  95
    |  ||        |  |  |   |    |  |  |   |  |  ||    ||| ||   |||     |
851 CAATACATGCTGTTTACCTCTATCTAGTAACAAATGTTTACATTTGTTAC 900

96 AGCTTCAAAGCTTGGATATTTTCTTGGCTGAACTCTACAAGCACCTTGAC 145
    ||    ||  |    |         ||       |         |       |   |   |||| 
901 TAGAGTAAGCTTTAGGGGTAGAACTTGAGTCTCAAAGCTCACGTCTTGGG 950

146 AGCAGCAGCAATGAGCGCCCAGACATTAGCTCCATCCAGAGACGGATTAA 195
    |    |    |    |        |       ||  |   |   ||                 |||  ||
951 AAAAAAAAAAGATCTGGTATTGATAGAACCT............TGATAAA 988

196 GAAAGTAACTCACGACATGGACATGTGCTACGGGATGATGGGAAG.CCTG 244
```

Table I-continued

Sequence Homologies between Human and Porcine SPAR cDNAs

```
             |     |  |||||    |||       |  |   |  ||  |||   ||
 989 TCCCTTGTTATAGCACATGTTTTTGTTTCCCAGAAGTAGGGCAAGAGCTC 1038

245 TTTCGCAGTGGCTCCCGGCAGACCCTCTTCGCCAGCCAGGTGATGCGGTA 294
     | | ||     |   |  ||     ||| |    |     | ||  |||
1039 TCTGGCTTATCCAATCAGCTTCTTCTCCTGACTTTAGTAGAGACACGGGC 1088

295 TGCCGATCTCTATGCAGCATCTTTCATCAATTTGCTGTATTACCCATTCA 344
     |  |   ||       | ||| |  ||  | ||   |||     |   |
1089 TTCATTACTGAGCTGGGAATTTAACTTCCCTCTGTCCTATGAAAAGTAGA 1138

345 GCTACCTCTTCAGAGCTGCCCACGTTTTGATGCCTCATGAGTCAACGGTG 394
     || | ||||   || |   |   | ||         ||    ||   |
1139 AGATTTTCCTAAGAGAAACCTTCAGTGAGAGCAGAACAGAAAAAAGAGCA 1188

395 GAACACACACATGTAGATATCAATGAAATGGAGTCCCCCCTCGCCACCAG 444
     |   ||  ||    || |       ||   |||    |  |     | |
1189 AAGAACTAACTGAAGGAGAGGGCAAGAAATCAGTGTAGTGTGGGGCAGCA 1238

445 GAACCGCACGTCC........GTGGATTTCAAAGATACCGACTACAAGCG 486
     |||   |  | |             |    |  |  | |||   |   |||
1239 GAAGGGAAGTGACAGGTCAAAGAAAATAGGAGAGAAAAGGAGAGAGAGCT 1288

487 GCATCAGTTGACACGGTCGATTAGTGAGATTAAACCCCCCAACCTCTTCC 536
     |   |||  |||  |      || ||   |       |     |    |
1289 ACCCAAGTAAACAGGAAAAGGGGAGGAAATACAGGGCAAAAGCAGAGAGC 1338

537 .....CACTGGCCCCCCAAGAA...................ATTACGCATT 563
          | ||||       |||||                    ||| | |
1339 AGGGGAATTGGCATGACAAGAAAGTGGTGAAACACAGAGGATTCCACCAG 1388

564 GCCATGATGAAGATGATGATGAAGAGGAGG......AGGAGGAAGAGGAA 607
     |  |    ||   | |   ||||||  ||       || |  |||||||
1389 ACAACAGAGAGCCCGGTAGAGAAGAGTGGGCTAGGATAAAGAGACAGGAA 1438

608 GAATGTGGTGGAAAACCAAAACTCTCAGCACTCATTAAACAAGTTCTGGC 657
     |   |||    ||  ||  |  |   |   |||  |  |  | ||   |
1439 ACAAATGGATTAAGACATAGAGTAGCCATTGTCAGTTACCTGGGTAAGAA 1488

658 GGGACTCACAGGAGCAAAGGCTGTCTCTCTGTGGGTCCTAGTGGGGGGTG 707
     ||| |        | ||            |   |||   |        |
1489 AAGATTGGTGGTCTAAATAAAATGCAGATTGTTCATTTACAATTCTGACT 1538

708 GGGGGCTCCATCAAAGGTACATCTTGGAAAGTTTTCTGAAGACTTTAAAA 757
     |        ||  | ||||||  ||||||  |    |    |    ||||
1539 GTTTAAATTATTTATGGTACACCTTGGTGCTTCACTTAATCATGTTAAGT 1588

758 TA...TTCTAATCATAGGGAGATACTTGTTTTAGTTTTTTGCATCTGCAC 804
     ||   ||  |||||| ||     |    ||  |||    ||  |
1589 TACAGTTGTAATCTTATTAATTACTTGCAACCAGCTTTCTCAATGTACCA 1638

805 TCTTT.....GCAGCTGGTTCAGAATTGTAAGAGAGTCTGTATCGGAGGA 849
     | |||     ||||| || ||  | |||           |   ||
1639 TGTATAGGGACAGCTTGTCAAGGGGTAGAAGTACTATAGCTTCACTTTT  1688

850 GAGGAAGGGTCAAGCGGGGCTGAACT..GCATGCAGCTGGCTCCGTTGTG 897
     |  || ||| | | |  | ||  ||   |||       |||     | |
1689 AATCCAGTATCATCCAGTACACAAATT-                     1738
     AGCCTTACACTGTTAGAATCTTTC

898 GTTTGTGACACTGTTTCATCATCAATATATCATAGTGTATCCAGAAACAC 947
     |     ||||| |  |  ||      || | | |  || ||  |  | ||
1739 CTGATGATGACTGGCTGAACTAAGCATTAGTCTTGACAATACAAGTACTG 1788
```

Table I-continued

Sequence Homologies between Human and Porcine SPAR cDNAs

```
 948 GAAGGGTGGTGGAGGGTCCCAGAGTGAAACAAAGACAATGGGAAGAGGTG  997
        |    |    |    |   ∩ ||   ||       ||      ||| |
1789 CTGTGCCCATTTACAGAAAGGGAAGCAATTCTTTCCCAGAAAGTAAGATA 1838

998 ATCCAAAAATGTTATGGTACAAATTGGGCTCTTACTACAAAAACCCATCT 1047
     ||||| | |||    || | |      |     |     | |   ||
1839 TGATTTAAATGCTTTGGCCTAATTAGTGTGAAAAAGGACATGGCCCAGG  1888

1048 TTTTCAGTGCATTACATAAGTATTGTATATCAGTGGAGAAATCTATTATT 1097
     |      |      | |      |   | ||   |       ||| |   |
1889 TAAGGCTTCAGGAAAAGCCAATTAACACATGTGCATATGTCTCTCTCCAT 1938

1098 TCCATGATCAAATGTAGTTTTTTGTTAAGGTCAAAGTTCTTTTACAAGCT 1147
     ||       |   |       |      || ||      ||        |        |
1939 TCACATCACCCAGCCTAGTCCAAGTCACCACCATCTCTTCACTTGCATTG 1988

1148 TTTAAGTGTCCTCAGGGACTCTGGGAAGGCTGCTGTCAGTGGCTCTGCAG 1197
     ||  |||    |||    |  | ||        |    |   | ||    |
1989 TTACAGTAGTCTCTTAGCCGCTTTTCCCACCTCCACCTTTGATATCTCTA 2038

1198 ACTGTTCTCTACTTACTATAGGGCTGGTCTGGAATGGACTGCAGTGATTT 1247
       |  |||     |     | | | | | | ||  |      |   || |||  |     |
2039 GTTATTCATGAGGTCCAAAATGACTTTTAAAAATAACACCACACTATCTC 2088

1248 CATTTTGAGCCAAAAATCTTCATCCACTTCTACATTTTTTTTAACCGATA 1297
        |||| ||       ||   |     |||||  |     |       |      | | |
2089 TATTTAGACTTTTCAACAGTTTCCCACTGCACAAGGGATACATTACCACA 2138

1298 GCAAAAATGCTTATTATCCAGAAACCTAGTCTTTTTCTTATCTAGGACGA 1347
        || | |       |          |  |  |||    |  ||||  |      ||
2139 AGGGAATTACACCAACTTGCCCTTGCAAATCTCATCTTTATGTTCAACTG 2188

1348 ATCTATAGAAAGGATTTCGCTGAAAGGACAAAGGAGCAAGCCACCCAAAA 1397
          ||              || || |     |     |    |       ||     ||    |  |
2189 TGCTGATCTTCATTTTCCTCCTCAGATGCGCAAATGCTTTCCCATCCCAG 2238

1398 GGAACAGAACCTCCTTCTTACACTGTAACTGACCAAAATT.CATTAGCGT 1446
     |||      |    |   ||||   | |    |        | ||| |    | |
2239 GGACTTCATGTTTGTTCTGCCCCAAAACTAAAACACTCTTCCCTGTTCTT 2288

1447 GGGCTGCATAGTGTGGCTTATGCCTGCCCCACTCCTCATTCCAGCCTTCT 1496
         |||  ||   ∩   ||     ||    |   || |||       | ||
2289 CATCTGGCTAACCAATATTTGTGCTTTCTGTGTCAGCATAAACACTGTTT 2338

1497 CTATCCTCCTGCTGTATTTCATATTCACGCATTAGAGGGTGGGAAGAGAT 1546
        ||   |      |    |      ||  || |         |||         ||| 
2339 TCCTCAGACAAGATTTCCTGACTCCCAGCCTAGCCAGGCCACTTCAAGGT 2388

1547 CTCTGGAAGCCAGAACTGCTACTCAAACGGAGGGCACAATGAGTGTGAAT 1596
      | ||   ||| ||    ||||        |         || |         |  |
2389 GTGTGCTCTCCATAAAGTTTACTTCTTCTATATACATCA.....ATTCAC 2433

1597 AAATTCACTGCAGAATCCCAAGTCACATCACTTCTTGTTGTTCTGAACAA 1646
     | | | |         ||| | |     || | ||   ||| ||    |
2434 ATAATTATACTTTAATACTTACTTGTAT.AATTGTTCGTGTGCTATGCCC 2482

1647 GAGTGCTGGATCATTACTGTATATTTTAAGGTATTATAACAGCCTCACCA 1696
        | |||  |       ||||            ||       |||       || |
2483 CCCAGTTGGCTGTAAGTCCTATAAAGACAGAGGCCACATCCATCTTGCAC 2532
```

Table I-continued
Sequence Homologies between Human and Porcine SPAR cDNAs

```
1697 GAACAGTGAAAGCTGTTACAACATTTTCCACAGTGGTGTAGACTCCTACT 1746
           ||  ||      |     |       |  |||    |||
2533 ATCCCTCTGTTCCTAGCACCTGCCATGGGTCCTATCAGCTGACAAGCACT 2582

1747 TTAACCTTCATATGTTTTTTCCAGTCTTACTGTCGTTTGTCAACATGGGA 1796
     |   |  ||||  |    | | | | |  |||  ||||||    |
2583 CAATATATTGTATGGATAAGTAAATATGATTCTAATTT.CCAACATCCTA 2631

1797 GGGTTGATTAGCTGTTCTAGAATT.......................... 1820
     ||| |||        |  |  |
2632 AACTTGTTTACAGTCCCACGGAGCCTGCTCAGGTAGAGCACATGCAATGC 2681

1298 GCAAAAATGCTTATTATCCAGAAACCTAGTCTTTTTCTTATCTAGGACGA 1347
     || | |        |          | | |||  |   ||||  |  ||
2139 AGGGAATTACACCAACTTGCCCTTGCAAATCTCATCTTTATGTTCAACTG 2188

1348 ATCTATAGAAAGGATTTCGCTGAAAGGACAAAGGAGCAAGCCACCCAAAA 1397
      ||          || | |    |   |   |    ||   ||    | |
2189 TGCTGATCTTCATTTTCCTCCTCAGATGCGCAAATGCTTTCCCATCCCAG 2238

1398 GGAACAGAACCTCCTTCTTACACTGTAACTGACCAAAATT.CATTAGCGT 1446
     |||       |  |  ||||   |  |     |    ||  |    |  |
2239 GGACTTCATGTTTGTTCTGCCCCAAAACTAAAACACTCTTCCCTGTTCTT 2288

1447 GGGCTGCATAGTGTGGCTTATGCCTGCCCCACTCCTCATTCCAGCCTTCT 1496
     |||  ||           ||   |  ||     ||  |||    |  | |
2289 CATCTGGCTAACCAATATTTGTGCTTTCTGTGTCAGCATAAACACTGTTT 2338

1497 CTATCCTCCTGCTGTATTTCATATTCACGCATTAGAGGGTGGGAAGAGAT 1546
       ||   |       |   |    ||  |   |       |||      ||  |
2339 TCCTCAGACAAGATTTCCTGACTCCCAGCCTAGCCAGGCCACTTCAAGGT 2388

1547 CTCTGGAAGCCAGAACTGCTACTCAAACGGAGGGCACAATGAGTGTGAAT 1596
     | ||     ||| ||    ||||       |          || |       | |
2389 GTGTGCTCTCCATAAAGTTTACTTCTTCTATATACATCA.....ATTCAC 2433

1597 AAATTCACTGCAGAATCCCAAGTCACATCACTTCTTGTTGTTCTGAACAA 1646
     | | | |         ||| |   | |     || | || ||  ||| ||    |
2434 ATAATTATACTTTAATACTTACTTGTAT.AATTGTTCGTGTGCTATGCCC 2482

1647 GAGTGCTGGATCATTACTGTATATTTTAAGGTATTATAACAGCCTCACCA 1696
     |  ||| |          ||||           ||     |  | |       | | |
2483 CCCAGTTGGCTGTAAGTCCTATAAAGACAGAGGCCACATCCATCTTGCAC 2532

1697 GAACAGTGAAAGCTGTTACAACATTTTCCACAGTGGTGTAGACTCCTACT 1746
           ||  ||      |     |       |  |||    |||
2533 ATCCCTCTGTTCCTAGCACCTGCCATGGGTCCTATCAGCTGACAAGCACT 2582

1747 TTAACCTTCATATGTTTTTTCCAGTCTTACTGTCGTTTGTCAACATGGGA 1796
     |   |  ||||  |    | | | | |  |||  ||||||    |
2583 CAATATATTGTATGGATAAGTAAATATGATTCTAATTT.CCAACATCCTA 2631

1797 GGGTTGATTAGCTGTTCTAGAATT.......................... 1820
     ||| |||        |  |  |
2632 AACTTGTTTACAGTCCCACGGAGCCTGCTCAGGTAGAGCACATGCAATGC 2681
```

Sequences corresponding to the two open reading frames were obtained and confirmed by complete double-stranded cDNA sequencing. The 32.3 kDa human and 32.8 kDa porcine ORFs are similar. Both show structural features consistent with cell membrane-bound receptors. SPAR ORF sequences are shown aligned in Table II.

TABLE II

Human SPAR and Porcine SPAR orf Sequence Homologies

```
  1 MRSKMTFKNNTTLSLFR......LFNSFPLHKGYITTRELHQLALANLIF  44
    |.:  .   ||||       ||.|  .:: : : ..: .| . :  :
  1 ....MDMCYGMMGSLFRSGSRQTLFASQVMRYADLYAASFINLLYYPFSY  46

45 MFNCADLHFPPQ...MRKCFPIPGTSCLFCPKTKTLF.............  78
    :|..|.: :|.:     :. ..| : .: :..:.:| .
 47 LFRAAHVLMPHESTVEHTHVDINEMESPLATRNRTSVDFKDTDYKRHQLT  96

79 .PVLHLANQYLCFLCQHKHCFPQTRFPDSQPSQATSRCVLSIKFTSSIYI 127
    .:  .:   . |   |...:.  . .:.   .|.:..:... |.  . |
 97 RSISEIKPPNLFPLAPQEITHCHDEDDDEEEEEEEEECGGKPK....... 139

128 NSHNYTLILTCIIVRVLCPPVGCKSYKDRGHIHLAHPSVPSTCHGSYQLT 177
    |..:|  .||..  .|.|.  . :. :        ...:. |..| |.
140 ........LSALIKQVLAGLTGAKAVSLWVLV......GGGGLHQRYILE 175

178 STQYIVWISKYDSNFQHPKLVYSPTEPAQVEHMQCFL.....CMCLQREE 222
    |   ::.. ||..: :  ||::         :   :  :::     :::  :|.:
176 S...FLKTLKYSNHREILVLVFC......ICTLCSWFRIVRESVSEERKG 216

223 REAL..LLLPRVTILTRLSAE.....STDERDGDSEPVNAVCRTALAFVP 265
    ..:|   :  |:..: ::|  :   :      ... |  .::...|..  :..:  .
217 QAGLNCMQLAPLWFVTLFHHQYIIVYPETRRVVEGPRVKQRQWEEVIQKC 266

266 HESNVMLGIHNLLIWLL.                                 282
    .:.|   |.... |:  :
267 YGTNWALTTKTHLFQCIT                                 284
```

The Garnier-Osguthorpe-Robson algorithm for estimating secondary structure predicts that pSPAR protein has a hydrophobic α-helix of 28 residues beginning at amino acid 48, consistent with a membrane-spanning region. It is followed by a turn, a second α-helix of 24 residues, then a series of turns and β-pleaded sheets. Human SPAR ORF has a 25 amino acid hydrophobic α-helix starting at residue 29, followed by β-pleated sheets and turns. Another 28 residue β-helix beings near amino acid 200. Thus, the projected secondary structure of hSPAR ORF is similar to that of its porcine counterpart.

pSPAR ORF is strongly homologous to several known cell membrane receptors as follows (in order of decreasing homology): acetylcholine, α-2c adrenergic, ryanodine, and progesterone receptors. It also resembles several cell membrane ATPases. Human SPAR is also homologous to membrane receptors and proteins, including insulin receptor, transforming growth factor-$b_1$-binding protein, and major histocompatibility antigens.

SPAR mRNA: Tissue Distribution and Distribution within the Lungs

RNA was prepared from organs of New Zealand White rabbits and BALB/c mice, slot-blotted to nitrocellulose, and probed with $^{32}$P-labeled 1.8 kb cDNA. Rabbits (FIG. 4) and mice make mRNA that hybridizes with pSPAR cDNA. This mRNA was expressed by in situ hybridization. Biotinylated 1.8 kb SPAR cDNA was used to detect SPAR transcripts in formalin-fixed tissues from normal mice. SPAR mRNA was seen in cells consistent in appearance and location with type II pneumocytes. It was also found in ciliated cells of the conducting airways (FIG. 5). Type I alveolar, pulmonary interstitial, and stromal cells were all negative. The alveolar cellular distribution of SPAR transcripts is similar to that of SP-B and SP-C (FIG. 5). Other tissues tested (liver, spleen, heart, kidney) did not express detectable SPAR. These results regarding SPAR mRNA detection are consistent with immunohistochemical experiments in which A2C and A2R were used to detect SPAR protein in tissue sections.

Effect of Antibody on Alveolar Surfactant Secretion

Pulmonary surfactant secretion from lung epithelial type II cells can be stimulated with a wide variety of agents including isoproterenol and ATP. Purified SP-A inhibits the secretion of lung surfactant in vitro. The effect of an antibody to an SP-A binding protein on type II cell membranes on surfactant secretion was tested. The results are shown in Table III.

TABLE III

| | % Lung Surfactant Secretion in 2 hours | |
|---|---|---|
| | − Antibody | + Antibody |
| Experiment 1: 50 ng/ml SP-A, 20 μg/ml antibody | | |
| ATP | 1.7 | 2.5 |
| ATP + SP-A, 50 ng/ml | 0.7 | 1.6 |
| Experiment 2: 50 ng/ml SP-A, 50 μg/ml antibody | | |
| ATP | 5.9 | 9.0 |
| ATP + SP-A, 50 ng/ml | 4.3 | 6.3 |

TABLE III-continued

|  | % Lung Surfactant Secretion in 2 hours | |
|---|---|---|
|  | − Antibody | + Antibody |
| Experiment 3: 100 ng/ml/SP-A 20 and 50 µg/ml antibody | | |
| ATP | 2.9 | 3.5 (20 µg/ml) |
|  |  | 3.1 (50 µg/ml) |
| ATP + SP-A, 100 ng/ml | 0.9 | 2.0 (20 µg/ml) |
|  |  | 2.4 (50 µg/ml) |

For each experiment shown in Table III, the top line indicates surfactant secretion without SP-A and the bottom line with SP-A, showing that SP-A inhibits secretion. The first column is without the antibody and the second column with the antibody. The data shows that the antibody promotes secretion (blocks the inhibition). Each experiment was conducted with a separate cell preparation. Experiments for each condition were conducted in duplicate and averaged to provide mean values. Each observation was within 10% of the mean value. These results indicated that this antibody may be a suitable agent to counteract in inhibition of secretion by SP-A.

The invention is further illustrated by the following, non-limiting examples.

EXAMPLES

Example 1

Proteins

Purified, recombinant human surfactant protein A was the kind gift of Dr. Mikko Hallman (Univ. of California, Irvine). *Staphylococcus aureus* protein A was purchased from Calbiochem. Procedures for radioiodination using chloramine T (Sigma) are well known in the art. For example see, D. S. Strayer, Hallman, M. and Merritt, T. A. (1991) *Clin. Exp. Immuno.*, 83, 41–46.

Monoclonal Antibodies

The production and characterization of A2C and A2R monoclonal anti-idiotype antibodies have been described (D. S. Strayer, *Am. J. Pathol.* 1991, 138, 1085–1095 and D. S. Strayer, *Biol. Neonat.* 1992, 61, 1–14). F344 rats were immunized with mixtures of rat monoclonal antibodies (MaAb) directed against porcine and rabbit surfactant proteins. Anti-idiotype antisera were assayed by inhibition of surfactant binding to anti-surfactant MaAb. Two different rats, each immunized against different combination of anti-surfactant MaAbs, produced detectable titers of anti-idiotype antibodies. Spleen cells from these rats were fused. Each fusion yielded one monoclonal anti-idiotype antibody that inhibited binding of surfactant protein to the respective anti-surfactant antibodies. A2C and A2R are thus independently derived anti-idiotype monoclonal antibodies, directed against other antibodies.

Tissues for Analysis

Organ tissues from normal female New Zealand White rabbits and normal female BALE/c mice (Jackson Laboratories) were removed aseptically and snap-frozen in liquid nitrogen. Tissues were homogenized (Polytron, Brinkmann Instruments) and RNA prepared (RNAzol, Cinna BioTex). Proteins from these tissues were solubilized and prepared for electrophoresis by boiling in 0.1% SDS, 50 mM 2-mercaptoethanol (Sigma).

Example 2

Screening of cDNA Libraries

Procedures used to screen cDNA libraries and purify phage-containing cDNAs encoding SP-A-binding proteins are well known in the art. Briefly, human and porcine lung cDNAs cloned into λgt11 as EcoRI fragments (Clontech) were grown, titered, and screened using Y1090 and Y1089 cells. Expression of proteins encodes by the cloned cDNA was induced by IPTG. Proteins were immobilized on PVDF membranes (Immobilon©, Millipore), which were then treated with A2R and A2C together, followed by rabbit anti-rat Ig (Melloy), and $^{125}$I-labeled Staphylococcus protein A. Positive plaques were purified by two cycles of plaque-to-plaque passage and retested at each step to ascertain that they produced a protein bound by A2R and A2C. Lysogenic colonies of Y1089 cells for expression of phage proteins were prepared according to well known protocols, *Current Protocols in Molecular Biology*, F. M., Ausubel et al. (Eds.) Wiley-Interscience, New York 1991, for example.

Example 3

SDS-PAGE and Protein Blotting

Proteins from tissues and bacteria were electrophoresed, blotted to Immobilon, and probed using A2C and A2R antibodies in accordance with known methods. When filters were probed with SP-A, a different protocol was used; such filters were treated with radiolabeled purified recombinant human SP-A using the same protocols and calcium-containing buffers reported by Y. Kuroki, Mason, R. J. and Voelker, D. R., *Proc. Natl. Acad. Sci. U.S.A.* 1988, 85, 5566–5570, to measure affinity of type II alveolar cells for SP-A. Binding of $^{125}$I-SP-A- was visualized by autoradiography.

Example 4

Restriction Digestion, Southern Plotting, and DNA Hybridization

DNA from phage and plasmids was digested with restriction enzymes (Promega) according to package inserts, electrophorese in (usually 1%) agarose gels and transferred to nitrocellulose. DNA probes were purified from low melting point agarose gels, labeled with $^{32}$P by random priming (Promega) and hybridized to these filter (hybridization, 42° C., 5×SSC, 50% formamide; final washes, 0.1×SSC, 52° C.).

Example 5

Cloning and Sequencing cDNA inserts encoding SP-A-binding proteins were cloned into pGEM3 as EcoRI fragments and sequences in accordance with well known methods. Briefly, after initial sequences were obtained using SP6 and T7 primers, 18-mer oligonucleotide primers 40 base pairs 5' to the last identified bases were used to prime sequencing reactions in both directions. Both DNA strands were completely sequenced in this fashion. Sequences were checked using an automated sequencer (Applied Biosystems).

Sequences were analyzed using DNA Inspector IIe (Textco). Protein (open reading frame (ORF)) secondary structure was analyzed using GCG software (Genetics Computer Group, Inc., Madison, Wis.) cDNA and protein sequences were compared with sequences reported to Gen-Bank and other data banks. The GenBank accession for hSPA cDNA is L10123. That for pSPAR cDNA is L10124.

Example 6

In Situ Hybridization

Normal mouse tissues were fixed immediately after excision in neutral buffered promalin, then embedded in paraffin.

Sections were mounted, rehydrated, and hybridized to cDNA probes using the AAP technique described by A. F. Guitteny, Bouque, B., Mougin, C., Teoule, R. and Bloch, B., *J. Histochem. Cytochem* 1988, 36, 563–571. Biotinylated cDNA probes were made from gel-purified cDNAs using biotinylated dUPT (Promega). cDNA probes for human SP-B and SP-C were kindly provided by Dr. Jeff Whitsett (University of Cincinnati, Ohio).

Example 7
Protocol for Pulmonary Surfactant Secretion Studies

For studies on pulmonary surfactant secretion, alveolar epithelial type II cells were isolated from lungs of specific pathogen free male Sprague-Dawley rats (180–200 grams body weight) according to well known methods. In brief, lungs were digested with elastase (3 units/ml), and the free cells were plated on IgG coated bacteriological tissue culture plates for 1 hour. The unattached cells were collected by "panning" and contained approximately 65% type II cells. These cells were suspended in minimum essential medium (MEM) containing 10% fetal bovine serum and plated on tissue culture plastic dishes. At this stage, 0.3 $\mu$Ci of [$^3$H-methyl]choline was added to the medium, and the cells incubated at 37° C. and in humidified air containing 5% $CO_2$ for the next 20–22 hours. During this period, type II cells attach to the plastic and the cellular lipids are labeled with radioactive choline. Using this protocol greater than 95% of the radioactivity in the phosphatidylcholine (PC) of lipid fraction is routinely recovered. At the end of the incubation period, the cells attached to tissue culture plates were washed five times, and fresh medium MEM without fetal bovine serum (1.5 ml) plated on the cells. To some of the plates, the antibody A2R was added at the indicated concentration. After incubation for 15 minutes, the indicated amount of SP-A (purified from rat lung surfactant) was added to some plates and all plates were incubated for another 15 minutes. At the end of 30 minutes of incubation, medium from 2 plates was removed, and analyzed for release of surfactant lipids during this 30 minute period (zero time). To other plates, 1 mM ATP or MEM (control) was added and incubation continued for the next 2 hours. At the end of this incubation, medium from each plate was removed, and both the cells and the medium for each condition were extracted for lipids after addition of egg PC as a carrier lipid and [$^{14}$C]-dipalmitoyl glycerophosphocholine as a tracer lipid to improve and correct for recoveries of surfactant lipids. The radioactivity in the lipid fractions was measured and corrected for recovery during lipid extraction which exceeded 90%. The surfactant secretion was then expressed as percent of total cellular phosphatidylcholine. (% Surfactant Secretion=radioactivity in the medium lipids× 100/radioactivity in the lipids of medium plus cells.) Results (Table III) are presented as secretion during 2 hours incubation and after subtraction of secretion during the first 30 minutes incubation.

Example 8

A2C and/or A2R may be used to target type II cells or bronchial epithelial cells that bear the SPAR antigen to deliver cytotoxic agents to these cells. The antibodies are either complexed to or are used to direct (e.g., via liposomes) a selected cytotoxic agent or radioactive agent and administered to an individual with a tumor of bronchial or type II cell origin. The antibodies may also be conjugated to a sensitizing agent which, when combined with another therapeutic modality, improves the specificity of the cytotoxic therapy for tumors of type II or bronchial epithelial cells. Methods of conjugating antibodies are well known in the art and selecting appropriate amounts and combinations of agents is well within the skill of the artisan. The "cytotoxic agent" may also include a gene or DNA fragment that could be used to control or direct cellular proliferation and/or gene expression.

Example 9

For diseases such as congenital alveolar proteinosis, in which it has been established that afflicted individuals are deficient in a surfactant protein, A2C and/or A2R may be used in gene therapy of type II cells. The surfactant protein B or its cDNA are cloned in accordance with well known methods, either downstream from its own promoter or from another promoter. The construct is targeted to type II cells-using liposomes or an engineered vector in which one or both of the antibodies is used to target the cells.

Example 10

For use in imaging, A2C and/or A2R is attached to a radiologically active substance such as $^{99m}$Tc for conventional imaging or $^{13}$C for MRI. The antibody is used to localize the radiologically active substance to type II cells. This localization is then quantitated or visualized in accordance with well known techniques by diagnostic radiologists or nuclear medicine physicians. In this way, it is possible to determine type II cell mass and/or distribution.

Example 11

A2C and/or A2R may be used to direct a modulating substance (stimulatory or inhibitory substance) such as TNF or PGE, to type II or bronchial epithelial cells. For example, a cytokine that stimulates surfactant production but is toxic to many cells at the needed concentrations is packaged in a vehicle which is attached to one or both antibodies. The vehicle-antibody combination allows delivery of the cytokine without adverse effects on other cells. Method of preparing compositions of modulating agents and vehicles are well known in the art.

What is claimed:

1. A method of increasing pulmonary surfactant secretion by alveolar cells comprising contacting an alveolar cell membrane with an effective amount of a composition comprising an antibody which binds to surfactant protein A receptor and blocking the binding of surfactant protein A to surfactant protein A receptor which increases the secretion of alveolar surfactant.

2. The method of claim 1 wherein the composition comprises a monoclonal antibody or a fragment of the monoclonal antibody containing an idiotype of surfactant protein A receptor antigen.

3. The method of claim 2 wherein said antibody comprises human constant regions.

4. The method of claim 2 wherein the monoclonal antibody comprises A2C, ATCC Deposit HB-12370, or A2R, ATCC Deposit HB-12369, monoclonal antibody or a fragment of the monoclonal antibody containing an idiotype of surfactant protein A receptor antigen.

5. An article of manufacture comprising packaging material and a pharmaceutical composition contained within said packaging material wherein said pharmaceutical composition comprises an antibody which binds to surfactant protein A receptor and blocks the binding of surfactant protein A to surfactant protein A receptor which increases the secretion of alveolar surfactant, wherein the pharmaceutical composition is formulated for intranasal, intratracheal and intrabronchial administration as an aerosol and wherein said packaging material comprises a label which indicates that said pharmaceutical composition can be used for the treatment of a condition characterized by insufficient production of alveolar surfactant.

6. The article of manufacture of claim 5 wherein the condition to be treated is respiratory distress syndrome.

7. The article of manufacture of claim 5 wherein the condition is alveolar proteinosis.

8. The article of manufacture of claim 5 wherein the pharmaceutical composition comprises A2C, ATCC Deposit HB-12370, or A2R, ATCC Deposit HB-12369, monoclonal antibody or a fragment of the monoclonal antibody containing an idiotype of surfactant protein A receptor antigen.

* * * * *